(12) United States Patent
Holladay

(10) Patent No.: US 11,298,263 B2
(45) Date of Patent: Apr. 12, 2022

(54) METHOD OF MITIGATING MYOPIA DEVELOPMENT AND RELATED INSTRUMENTATION

(71) Applicant: Jack T. Holladay, Bellaire, TX (US)

(72) Inventor: Jack T. Holladay, Bellaire, TX (US)

(*) Notice: Subject to any disclaimer, the term of this patent is extended or adjusted under 35 U.S.C. 154(b) by 281 days.

(21) Appl. No.: 16/513,132

(22) Filed: Jul. 16, 2019

(65) Prior Publication Data
US 2021/0015664 A1 Jan. 21, 2021

(51) Int. Cl.
| | | |
|---|---|---|
| *A61F 9/00* | (2006.01) | |
| *A61F 9/007* | (2006.01) | |
| *A61B 3/103* | (2006.01) | |
| *A61N 5/06* | (2006.01) | |
| *A61B 3/117* | (2006.01) | |

(52) U.S. Cl.
CPC .......... *A61F 9/00736* (2013.01); *A61B 3/103* (2013.01); *A61F 9/0008* (2013.01); *A61F 9/0079* (2013.01); *A61N 5/0601* (2013.01); *A61N 5/062* (2013.01); *A61B 3/117* (2013.01); *A61M 2210/0612* (2013.01); *A61N 2005/0651* (2013.01); *A61N 2005/0658* (2013.01)

(58) Field of Classification Search
CPC ....... A61F 9/0008; A61F 9/0079; A61F 9/008
USPC ...................... 606/2–6; 607/88–89
See application file for complete search history.

(56) References Cited

U.S. PATENT DOCUMENTS

| | | |
|---|---|---|
| 7,727,544 B2 | 6/2010 | Schwartz et al. |
| 8,580,789 B2 | 11/2013 | Krueger et al. |
| 9,005,099 B2 | 4/2015 | Blumenkranz et al. |
| 9,125,856 B1 | 9/2015 | Paik et al. |
| 2008/0114283 A1* | 5/2008 | Mattson ................. A61K 31/00 604/20 |
| 2012/0209051 A1* | 8/2012 | Blumenkranz ......... A61P 27/02 600/2 |
| 2020/0187771 A1* | 6/2020 | Yun ...................... A61B 3/0025 |

FOREIGN PATENT DOCUMENTS

| | | |
|---|---|---|
| CN | 204521168 | 8/2015 |
| RU | 2558997 | 8/2015 |
| RU | 161371 | 4/2016 |

OTHER PUBLICATIONS

Wang J, Li Y, Jin Y, Yang X, Zhao C, Long Q. Corneal Biomechanical Properties in Myopic Eyes Measured by a Dynamic Scheimpflug Analyzer. J Ophthalmol. 2015;2015:161869. doi: 10.1155/2015/161869 (Year: 2015).*

(Continued)

*Primary Examiner* — John R Downey
(74) *Attorney, Agent, or Firm* — Patterson Thuente Pedersen, P.A.

(57) ABSTRACT

A method of mitigating the development of myopia, includes measuring elasticity of collagen of an eye; identifying an eye for which the elasticity measured is above a preselected threshold; selectively applying a collagen cross-linking reagent proximate collagen of a sclera of a posterior pole portion of the eye for which the elasticity measured is above the preselected threshold; and irradiating at least the posterior pole portion of the eye with radiation of an appropriate wavelength to initiate covalent bonding and cross-linking of the collagen for which the elasticity measured is above the preselected threshold.

20 Claims, 9 Drawing Sheets

(56) References Cited

OTHER PUBLICATIONS

Dotan A, Kremer I, Livnat T, Zigler A, Weinberger D, Bourla D. Scleral cross-linking using riboflavin and ultraviolet-a radiation for prevention of progressive myopia in a rabbit model. Exp Eye Res. Oct. 2014;127:190-5. doi: 10.1016/j.exer.2014.07.019. Epub Aug. 8, 2014. PMID: 25111424. (Year: 2014).*

Campbell et al., "Qauntification of the efficacy of collagen cross-linking agents to induce stiffening of rat sclera," J. R. Soc. Interface 14, 2017, 9 pages.

Chu et al., "The Effects of Scleral Collagen Cross-Linking Using Glyceraldehyde on the Progression of Form-Deprived Myopia in Guinea Pigs," Journal of Ophthalmology, 2016, 8 pages.

Elsheikh, "Is sclera cross-linking a feasible treatment for myopia control?" Ophthalmic & Physiological Optics, 33 (2013), pp. 385-389.

Liu et al., "Scleral Cross-Linking Using Riboflavin UVA Irradiation for the Prevention of Myopia Progression in a Guinea Pig Model: Blocked Axial Extension and Altered Scleral Microstructure," Nov. 9, 2016, 10 pages.

Norman et al., "Dimensions of the human sclera: Thickness measurement and regional changes with axial length," Experimental Eye Research, vol. 90, 2010, pp. 277-284.

Parks, "Extraocular Muscles," Clinical Ophthalmology, vol. 1, Chapter 1, pp. 1-12, prior to Jul. 16, 2019.

Parks, "Eye Movements and Positions," Clinical Ophthalmology, vol. 1, Chapter 2, pp. 1-9, prior to Jul. 16, 2019.

Parks, "Vergence" Clinical Ophthalmology, vol. 1, Chapter 7, pp. 1-7, prior to Jul. 16, 2019.

Zhang et al., "A Review of Collagen Cross-Linking in Cornea and Sclera," Journal of Ophthalmology, 2015, 12 pages.

Zyablitskaya et al., "Evaluation of Therapeutic tissue Crosslinking (TXL) for Myopia Using Second Harmonic Generation Signal Microscopy in Rabbit Sclera," Investigative Ophthalmology & Visual Science, vol. 58, No. 1, Jan. 2017, pp. 21-29.

\* cited by examiner

METHOD OF MITIGATING MYOPIA DEVELOPMENT AND RELATED INSTRUMENTATION

TECHNICAL FIELD

Embodiments of the invention generally relate to the eye, ocular anatomy and refractive error. More specifically, embodiments of the invention relate to myopia development/progression and techniques that may mitigate or limit myopia development/progression.

BACKGROUND

It is understood that myopia generally occurs because the axial length of the globe of the eye is excessively long as compared to the focusing power of the optical parts of the eye. This is largely based on statistical studies that compare axial length and refractive power of myopic and non-myopic eyes. The general anatomy of the human eye is that of a roughly prolate ellipsoid (approximately football shaped) structure, the outer shell of which is formed of substantially of collagen and includes the cornea and sclera. Within the sclera lies the choroid which is a spongy layer of blood vessels that provides most of the blood supply to the retina which lies inside the choroid. Bruch's membrane which is the innermost layer of the choroid is a brittle minimally stretchable structure. The retina is the innermost layer of the eye and the structure of the eye that houses the rod and cone cells which are actually sensitive to light. The retina is analogous to the film in a camera or the sensor in digital camera.

Many decades of research have been directed toward attempting to understand how myopia develops and why myopia progresses for some individuals. It has long been suggested that reading and focusing at near somehow encourages the development and progression of myopia by causing elongation of the eye. The act of focusing for near is referred to as accommodation. Accommodation occurs because of the elasticity and flexibility of the crystalline lens within the eye. The crystalline lens is suspended under tension by fibers called zonules within a ring formed by the ciliary muscle. To focus at near, the ciliary muscle contracts thus reducing its diameter and tension on the lens zonules. The lens then becomes thicker and more curved to provide additional focusing power.

It has been theorized that accommodation leads to increased pressure within the globe of the eye and may in some way encourage the globe of the eye to stretch thereby increasing the axial length of the eye and contributing to the development of myopia. Research has not however shown substantial evidence to support this theory.

The eye is housed within the orbit which consists of the orbital bones and contains a layer of fat which supports the eye. The orbit is roughly cone-shaped. The globe of the eye is located proximate a base of the cone while the optic nerve exits the orbit proximate the apex of the cone on its way to the brain. The eye is additionally protected by the eyelids. The eye is suspended within the orbit in part by forces applied by the four rectus muscles which pull the eye backward against the fat pad that closely surrounds the eye. The four rectus muscles include the superior rectus, inferior rectus, lateral rectus and medial rectus. The insertions of the rectus muscles are located on the globe forward of the equator. In addition, two oblique muscles exert force on the eye generally rotationally and forwardly. The insertions of the oblique muscles are located in the globe posterior to the equator. The superior oblique generally abducts, depresses and internally rotates the eye via the trochlea. That is turns the eye outward, downward and torsionally inwardly at the top. The inferior oblique generally causes abduction, elevation and extorsion of the globe. That is turns the eye outward, upward and torsionally outwardly at the top.

SUMMARY

Embodiments of the invention are expected to solve many of the above problems and include a method of mitigating myopia development as well as instrumentation for techniques to apply the method.

It is believed by the inventor that the convergence associated with near viewing that it is involved in reading and close work is a mechanistic factor in the development of progression of myopia. Reading and viewing close objects requires two things. First, the eyes must be focused at the appropriate distance to see the near object clearly. This is accomplished by the act of accommodation in which the ciliary body of the eye contracts thereby reducing its inner diameter and releases tension on the lens zonules that support the crystalline lens within the eye. When tension on the lens zonules is relaxed the resiliency of the crystalline lens causes it to reduce in diameter and increase in thickness thus increasing its focusing power and focusing the eye at an appropriate distance to see the near object or reading material. Second, the eyes must converge or turn inward to both point at the near object so that the near object is seen singly. It is well known to those of skill in the art that this relationship includes accommodative convergence. That is, when one focuses the eye at a certain distance, the eyes also converge to a certain degree to approximate single vision at that distance. Other convergence effort is often used to achieve single, binocular vision at near.

Generally, when convergence is referred to in this application, it refers to turning inwardly of the eyes to attain single binocular vision of an object located within approximately one meter of the viewer.

Convergence is accomplished largely by contraction of the medial rectus muscles which pull the eyes inward and a consequent relaxation of the lateral rectus muscles. It is understood under Sherrington's law of reciprocal innervation which postulates that contraction of one muscle results in relaxation of its opposing counterpart. Because reading generally also involves looking downward, the aiming of the eyes during reading and close work also involves contraction of the superior oblique extraocular muscles and relaxation of the inferior oblique extraocular muscles.

It is understood that the extraocular muscles include both quick response muscle fibers and slower tonic response muscle fibers. The tonic response fibers are more involved in sustained effort of the medial recti during sustained accommodation and convergence. Limiting our consideration to the lateral and medial rectus muscles for the moment, when the medial rectus muscles contract force is transferred through the globe of the eye as a tensile force between the insertion of the medial rectus and the annulus of Zinn. From the medial rectus insertion on the globe of the eye a tensile force is transferred through the sclera in the vicinity of the ciliary body to the limbus of the cornea on the medial side then through the cornea itself to the limbus on the lateral side and to the sclera on the lateral side. It is generally believed that the temporal sclera is thinnest at or near the equator of the eye and thicker at the lamina cribrosa.

It is commonly believed that the act of accommodation somehow contributes to the development of myopia for at least some people. However, no clear mechanism for the alleged link between accommodation and myopia development has been generally elucidated and accepted. Furthermore, studies using atropine to fully relax accommodation have also shown very little to no benefit. It is Applicant's position that the mechanism of myopia development is based, at least in part, on the convergence required to view near objects, rather than accommodation.

In order to view near objects clearly and binocularly, it is necessary to do two things. An individual must focus for the appropriate distance and must converge the eyes to aim at the near object so that the object is seen singly. Convergence occurs primarily because of contraction of the medial rectus muscles as well as some action by the superior and inferior oblique muscles. In addition to convergence individuals generally tend to aim the eyes downward when viewing near objects. Accordingly, the actions of the medial rectus apply tension to the nasal sclera forward of the insertion of the medial rectus. This tension is transmitted through the nasal sclera to the nasal limbus, then to the cornea, then to the temporal limbus and then temporal sclera posteriorly to the posterior pole of the eye and as far as the lamina cribrosa through which the optic nerve exits the back of the eye. The superior and inferior oblique muscles tended to apply tension generally to the posterior pole of the eye because of the anatomical location of their insertions.

The inventor has recognized that stretching of the sclera particularly in the posterior pole and temporal regions of the eye is a major contributor to the development and progression of myopia. The mechanism of this stretching is based on the tension applied to the temporal and posterior pole sclera by the act of convergence. Convergence applies a substantial tensile force to the posterior pole portion and temporal portion of the sclera thereby creating a stretching force on the collagen that forms the sclera.

Accordingly, according to some embodiments the invention, collagen cross-linking is utilized to minimize scleral stretching particularly, in the vicinity of the macula proximate the posterior pole and temporal sclera. The portion of the globe that is the weakest link from the insertion of the medial rectus to the lamina cribrosa is the posterior pole and temporal equatorial sclera. Because of the elliptical shape of the globe, the steeper radius of the posterior pole causes a greater tensile force on the exterior scleral layers. In addition, the lateral rectus muscle provides some support to the equatorial temporal sclera due to its intimate contact in this region. In addition, the four rectus muscles form a cone which originates at the annulus of Zinn. The insertions of the four rectus muscles are just posterior to the limbus and anterior to the equator. Thus the four rectus muscles support the equatorial sclera along with Tenon's capsule. The cone of the rectus muscles forms a space behind the posterior pole of the globe of the eye providing little or no support in this region. This coincides with the region of the maximum combined tensile stress from the oblique muscles and from the medial rectus when the eyes undergo convergence.

In the vicinity of the macula, the sclera is somewhat thicker than at the equator but it is recognized by the inventor that the sclera at the posterior pole is under greater tensile stress than other portions of the eye during convergence. This is apparent and can be seen because of the development of lacquer cracks in individuals with advanced myopia in the macular region. Lacquer cracks, which are visible upon ophthalmoscopy, represent breaks in Bruch's membrane that are caused by stretching of the sclera and choroid. While the sclera and choroid can stretch, Bruch's membrane is not elastic and therefore cannot stretch along with the other structures. Thus, breaks in Bruch's membrane occur which are recognized as lacquer cracks. Lacquer cracks occur in the posterior pole but are rarely, if ever, seen in the equator region. This is further evidenced by observation of the retinal pigment epithelium. When the retinal pigment epithelium lacks support from the tissues exterior to it, scarring of the retinal pigment epithelium and Fuchs spot may occur. In cases of severe advanced myopia, vision loss secondary to damage to the photoreceptors occurs because of damage to the retinal pigment epithelium. In short, the stretching progresses inwardly from the exterior sclera, to interior sclera, to the choroid, Bruch's membrane and then to the cones of the macular region of the retina.

Certain aspects of the prior art suggest treatment of the sclera by collagen cross-linking in the vicinity of the equator of the eye. However, physiologically and visually, the inventor notes that the macular area of the retina and the posterior pole is more important to vision than is the equatorial retina and lacquer cracks are never seen in the equator region. According to an example embodiment of the invention treatment in the posterior pole and temporal sclera tends to protect against breaks in Bruch's membrane and the retinal pigment epithelium. This in turn is expected to prevent damage to the photoreceptors in cases of advanced progressive myopia. According to aspects of the invention the macula should be protected from damage to mitigate potential vision loss. In addition, the cross-linking is expected to reduce the elongation of the eye, reducing the progression of axial myopia, in much the same manner as cross-linking reduces progression of keratoconus, by reducing elasticity of the collagen fibers.

According to another example embodiment of the invention, to minimize or mitigate the effect of convergence as the underlying mechanism of myopia development, corrective lenses can be prescribed, including, for example, between ten and twelve prism diopters of base in prism prescribed to children to mitigate the need for convergence. This approach permits children to accommodate for near vision but mitigates the requirement for convergence. This effect is the opposite of current trials relaxing accommodation with atropine or other cycloplegics.

Applicant acknowledges that this approach may raise a concern of the development of strabismus because of encouraging convergence insufficiency. However, it is known that convergence insufficiency can be treated successfully and relatively easily by orthoptic techniques, visual training including the simple technique of pencil push-ups to improve convergence ability. It is thus the inventor's position that possible development of convergence insufficiency in children is a relatively small price to pay for mitigating the development of progressive myopia in children.

It is well known that there are genetic factors that affect the development of myopia. The children of myopic parents are more likely to be myopic to the children of parents who are not myopic and children in China currently have a much higher probability of having progressive myopia than in Europe and the United States. In addition to these factors, the inventor has observed that the elasticity of collagen in the human body varies. It is true however, that elasticity of collagen decreases with age due to normal cross-linking that occurs in the body with aging. Even though collagen is more elastic in children, there is still a variation from one child to the next which is genetic. This is probably due to genetic factors different from those that are commonly implicated in myopia development which relate more to genetically determined axial length of the eye. In some individuals collagen is weaker or more elastic than others and it is believed that those individuals who have a genetic predisposition to myopia related to a tendency to develop a longer axial length and the eye and who also have a tendency toward more elastic or weaker collagen are likely those that go on to develop severe progressive myopia. This occurs in combination with the genetic tendency of some individuals to develop myopia because of the globe of the eye becoming longer with age, just as some youth grow taller with age. The globe being relatively larger as related to the optical power of the optical parts of the eye leads to myopic defocus. The tendency of some individuals to have more stretchable collagen than others also likely contributes to lengthening of the eye.

Testing instruments such as the Corvis from Oculus and Reichert's Ocular Response Analyzer (ORA) are available to evaluate the elasticity of collagen in the eye. According to example embodiments of the invention, such instruments can be used to predict which individuals are likely to benefit from collagen cross-linking of the posterior pole and temporal portions of the sclera according to other example embodiments of the invention. It should be understood that corneal collagen is the same as scleral collagen in its chemical structure. The cornea is transparent while the sclera is opaque because of the particular alignment of collagen fibrils in the cornea. Accordingly, measuring the elasticity of the corneal collagen is expected to be predictive of the elasticity of scleral collagen.

The Ocular Response Analyzer (abbreviated ORA) was originally developed with the intent of the testing for the development of keratoconus but has since been demonstrated to measure elasticity of the eye and its collagen. The ORA instrument operates in a fashion similar to an air puff tonometer and effectively measures corneal and scleral hysteresis. When the force of the air puff is applied against the cornea there is a transient increase in intraocular pressure that creates distortion of the entire globe of the eye. Subsequent research has demonstrated that the best correlation between the measurements of this instrument is with open angle glaucoma rather than with keratoconus. It is believed that this correlation with open angle glaucoma is because stretching of the sclera in the vicinity of the lamina cribrosa both bends and distorts axons of the optic nerve thus creating a mechanism by which the optic nerve axons are harmed that contributes to the optic nerve damage known to occur in open angle glaucoma which leads to vision loss. As mentioned above, another instrument that can be utilized to measure collagen elasticity is designated the Corvis instrument by Oculus. It is used to measure deflection of the cornea.

According to one example embodiment, the invention includes a method of mitigating the development of myopia, including measuring elasticity of collagen of an eye; identifying an eye for which the elasticity measured is above a preselected threshold; selectively applying a collagen cross-linking reagent proximate collagen of a sclera of a posterior pole of the eye for which the elasticity measured is above the preselected threshold; and irradiating at least the posterior pole of the eye with radiation of an appropriate wavelength to initiate covalent bonding and cross-linking of the collagen for which the elasticity measured is above the preselected threshold. For example, for riboflavin a wavelength of 370 nm is typically applied.

According to another example embodiment, the method further includes measuring the elasticity of the collagen of the eye utilizing an ORA instrument.

According to another example embodiment, the method further includes measuring the elasticity of the collagen of the eye utilizing a Corvis instrument.

According to another example embodiment, the method further includes irradiating at least the posterior pole of the eye by inserting an instrument exterior to the sclera and directing the radiation of the appropriate wavelength toward the sclera of the posterior pole.

According to another example embodiment, the method further includes irradiating at least the posterior pole of the eye by directing radiation into the eye and then from within the eye to the sclera.

According to another example embodiment, the method further includes applying the collagen cross-linking reagent by infusing the reagent into the orbit by intra-orbital injection.

According to another example embodiment, the method further includes selecting the collagen cross-linking agent from a group consisting of riboflavin, genepin, nitroalcohols, glyceraldehyde paraformaldehyde, and glutaraldehyde, for example.

According to another example embodiment, the method further includes genetic testing of an individual or an individual's family members to determine a risk of stretchable collagen and thus progressive myopia. According to example embodiments of the invention, this may include considering parental family history and/or genetic origin as well as DNA evaluation that identifies those at risk as an adjunct to the measurement of elasticity of collagen.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
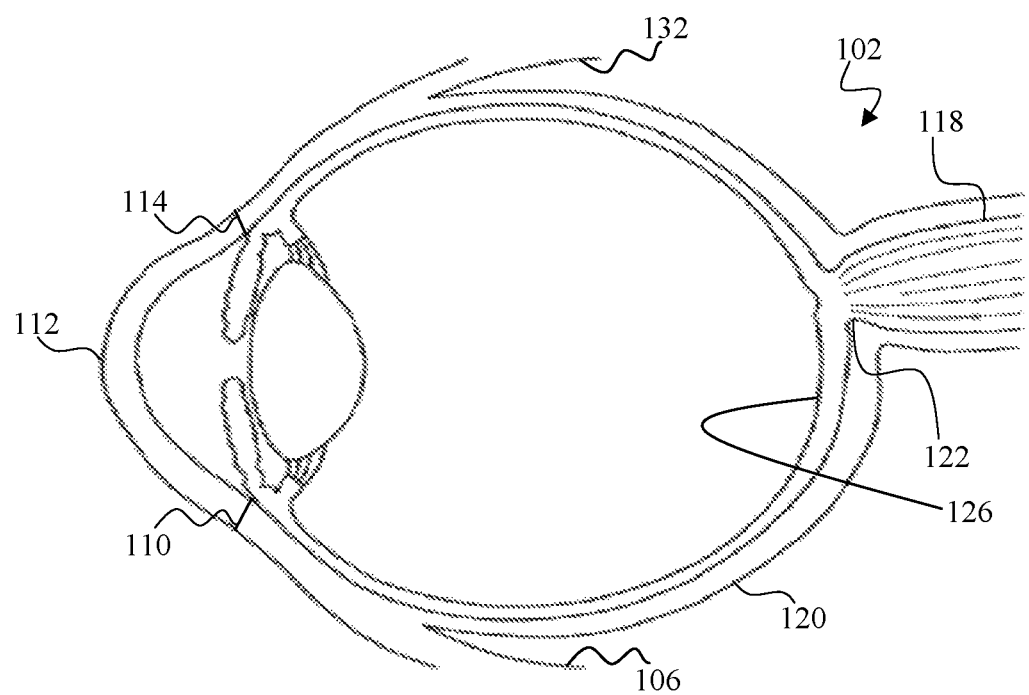
FIG. 1 is a superior cross-sectional view of an eye.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 5:
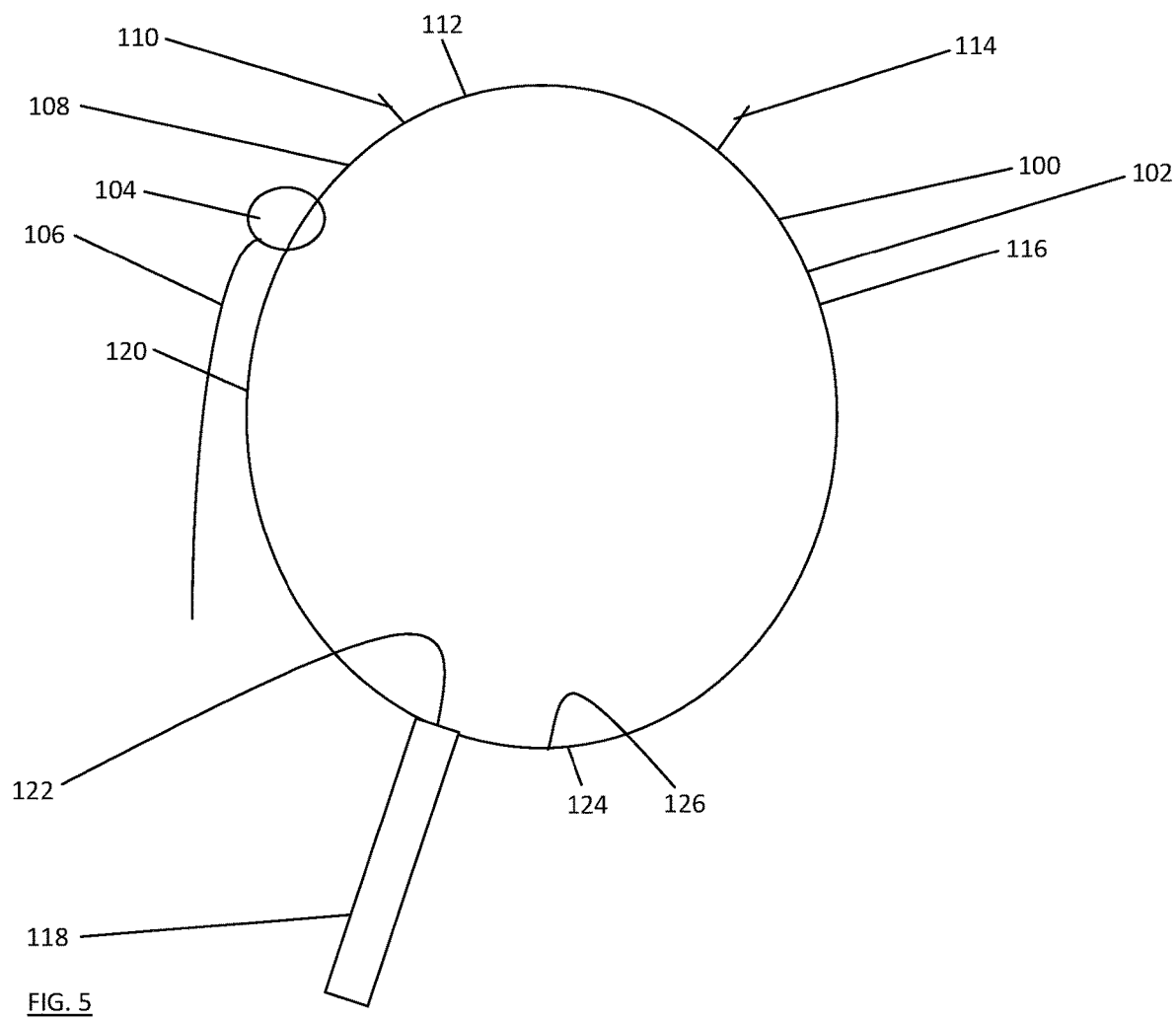
FIG. 5 is a schematic view of an eye.

Referring to FIG. 5, a schematic view of a right eye from above is depicted. Globe 100 of eye 102 is depicted along with insertion 104 of medial rectus 106. Globe 100 generally has the shape of a prolate ellipsoid. First scleral portion 108 extends between the insertion 104 of medial rectus 106 and nasal limbus 110. Cornea 112 extends between nasal limbus 110 and temporal limbus 114. Second scleral portion 116 extends from the temporal limbus 114 to a vicinity of optic nerve 118 which penetrates sclera 120 at lamina cribrosa 122. Posterior pole 124 is located temporally of optic nerve 118. Posterior pole 124 generally coincides with an internal location of macula 126. Macula 126 contains a high concentration of retinal cone cells which are responsible for detailed central vision and color vision.

Upon contraction of medial rectus 106, tension is applied to insertion 104. Tension is transmitted from insertion 104 through first scleral portion 108 to nasal limbus 110. Tension is further transmitted from nasal limbus 110 through cornea 112 to temporal limbus 114. Tension is further transmitted from temporal limbus 114 through the second scleral portion 116 and ultimately to posterior pole 124.

Applicant has recognized that this tension applied to posterior pole 124 and second scleral portion 116 tends to stretch posterior pole 124 and second scleral portion 116 thereby tending to increase the length of the eye 102. This portion of globe 100 forms the weakest portion of the globe because of the elliptical shape of globe 100 and the steeper radius of curvature of the posterior pole 124 portion and second scleral portion of globe 100. The steeper radius causes there to be greater tensile force applied to the exterior sclera.

Figure 2:
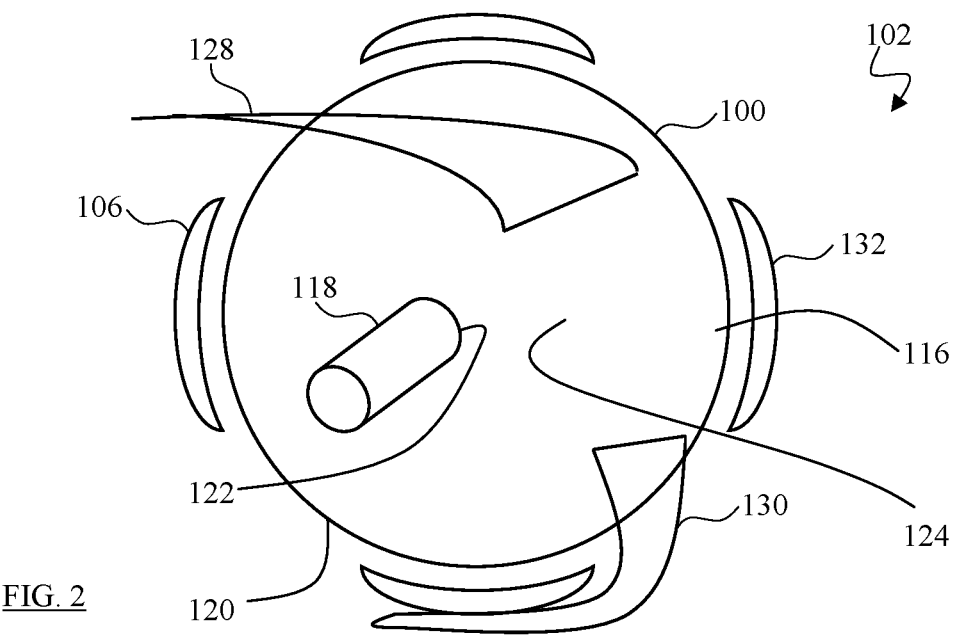
FIG. 2 is a posterior perspective schematic view of an eye including depiction of the optic nerve the superior oblique and the inferior oblique muscles

Referring now to FIG. 2, a view of the posterior aspect of the eye is depicted. In addition superior oblique 128 has its insertion generally above posterior pole 124 and abducts, depresses and internally rotates the eye. Inferior oblique 130 has its insertion generally below posterior pole 124 and when it contracts causes extorsion, elevation and abduction of the eye. Accordingly, contraction of superior oblique 128 and opposing relaxation of inferior oblique 130 applies tension to posterior pole 124 as eye 102 is rotated downwardly as commonly occurs in concert with convergence and accommodation during reading or close work. Applicant recognizes that this tension, in addition to the tension applied to posterior pole 124 and second scleral portion 116, tends to stretch posterior pole 124 and second scleral portion 116. This is in addition to the tension discussed above with relation to convergence or accommodative convergence.

Example embodiments of the invention include methods of mitigating myopia development/progression.

Figure 3:
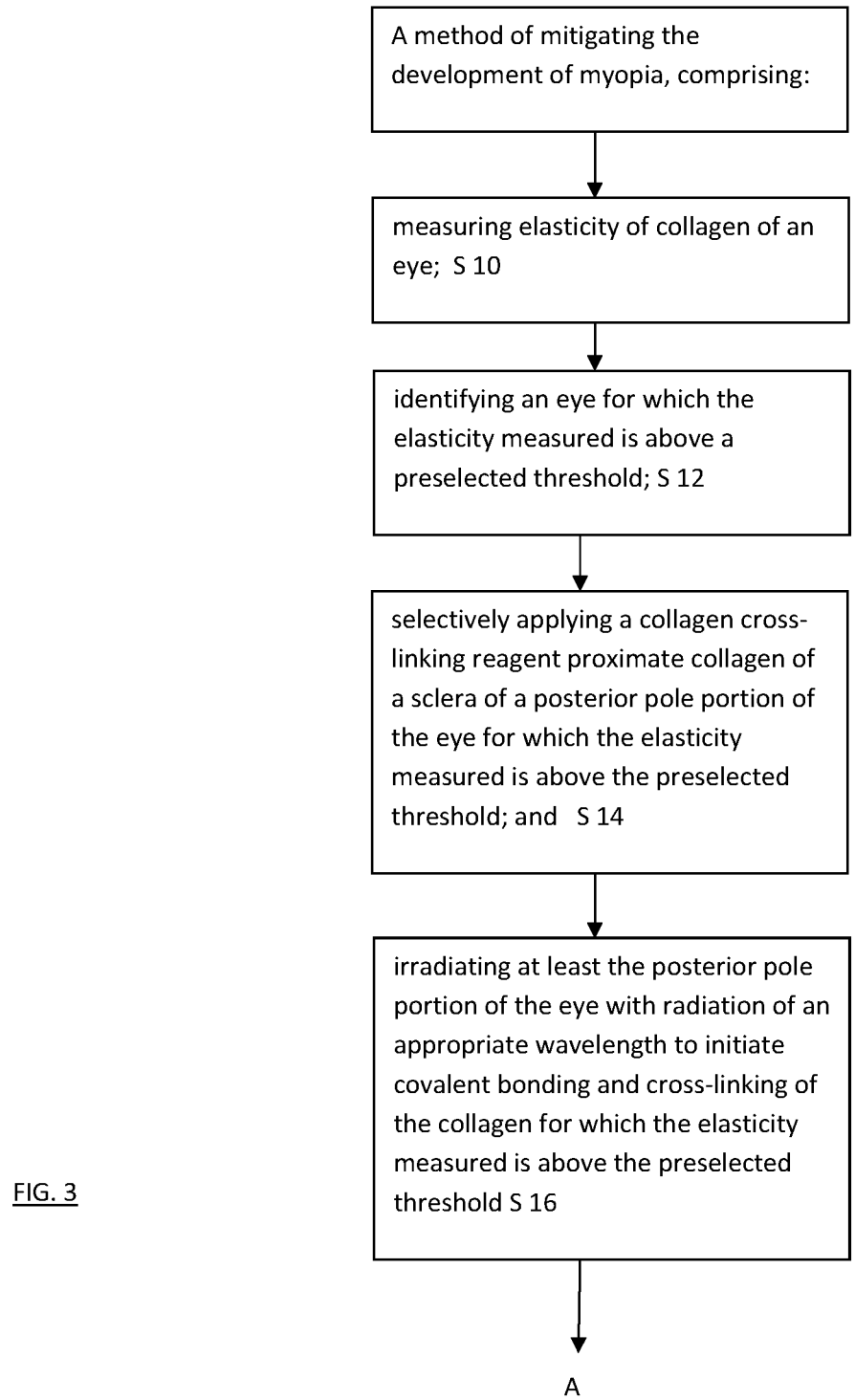
FIG. 3 is a flowchart of a method according to an example embodiment of the invention.
Figure 3:
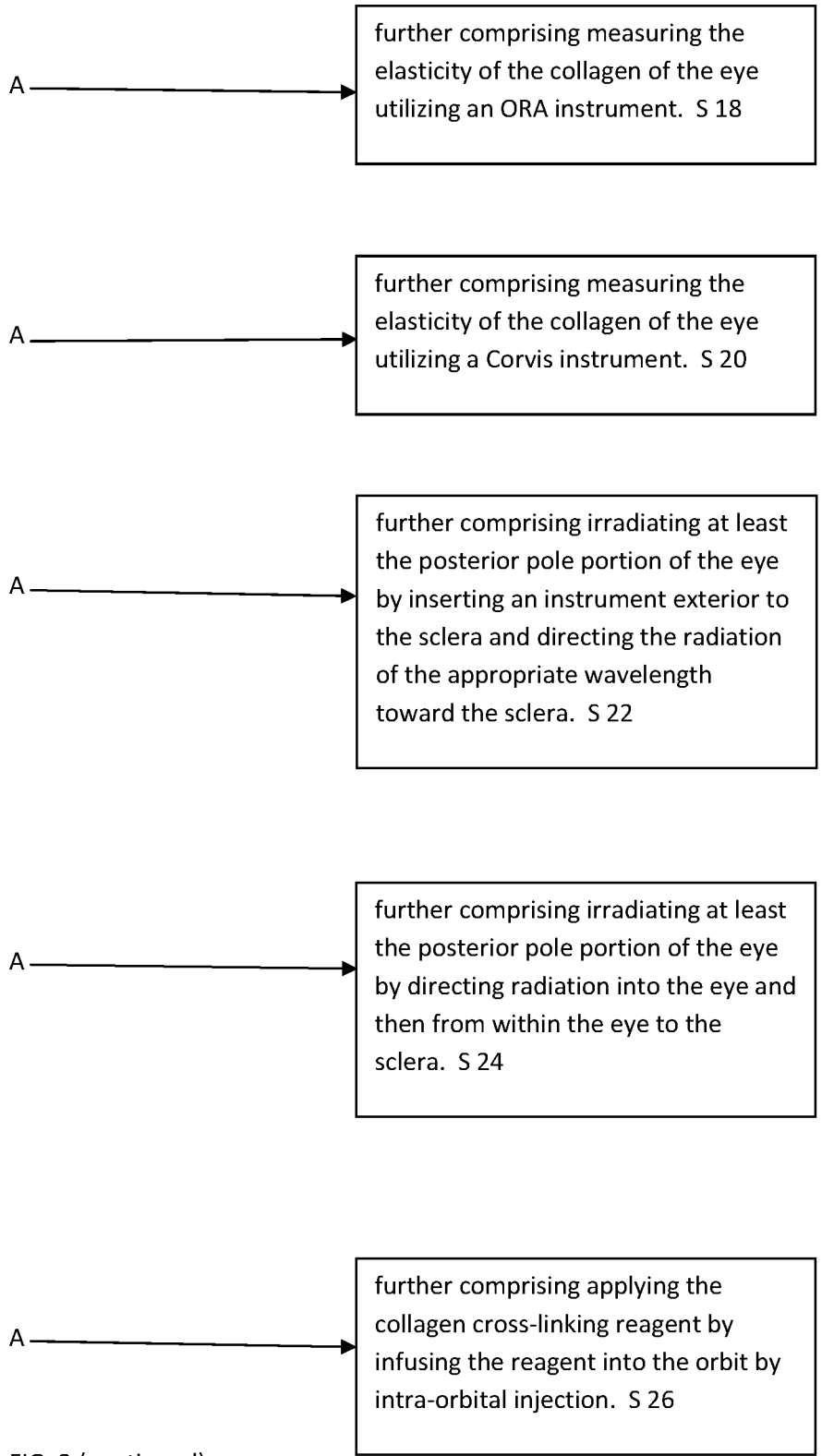
Figure 3:
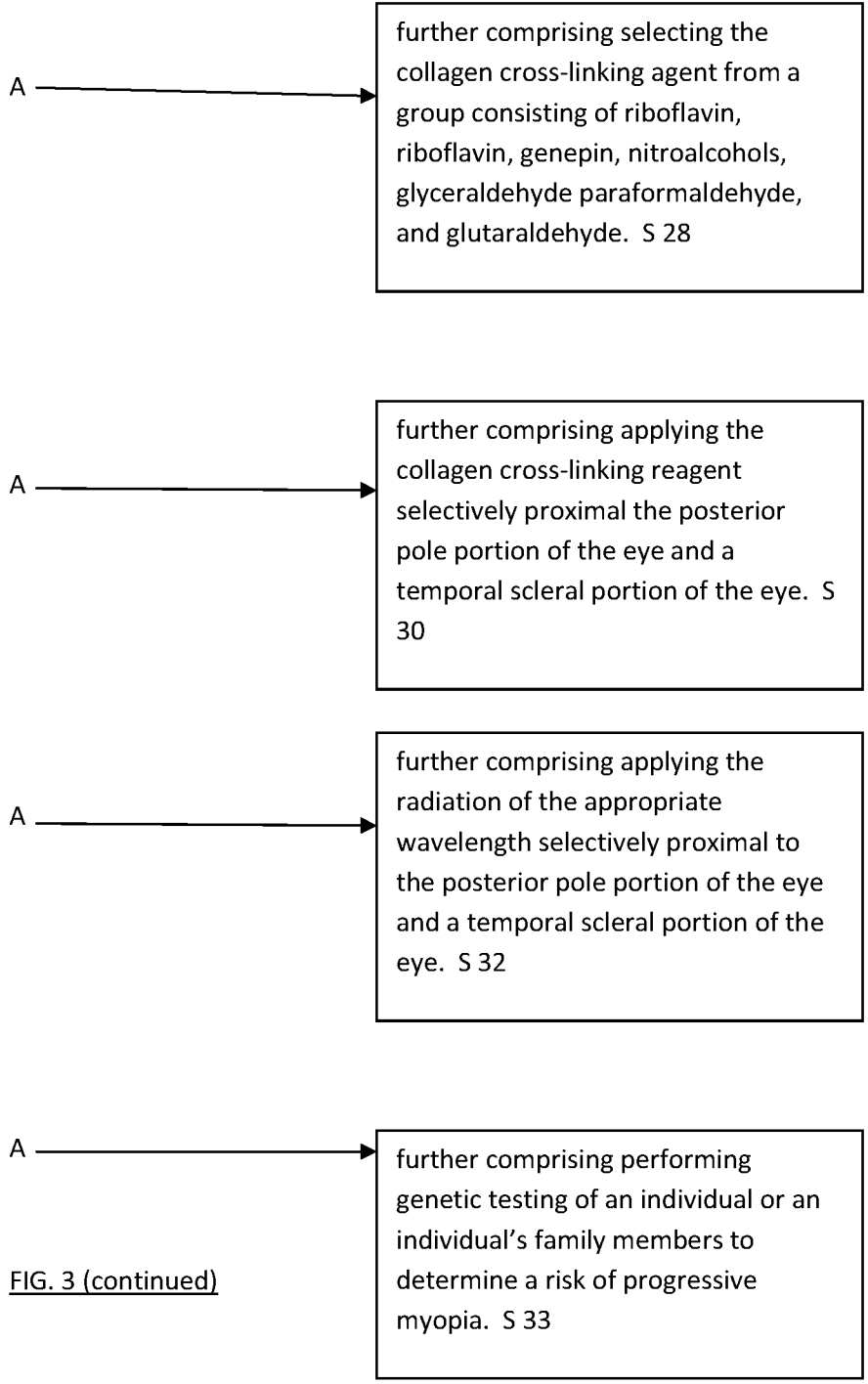
Figure 4:
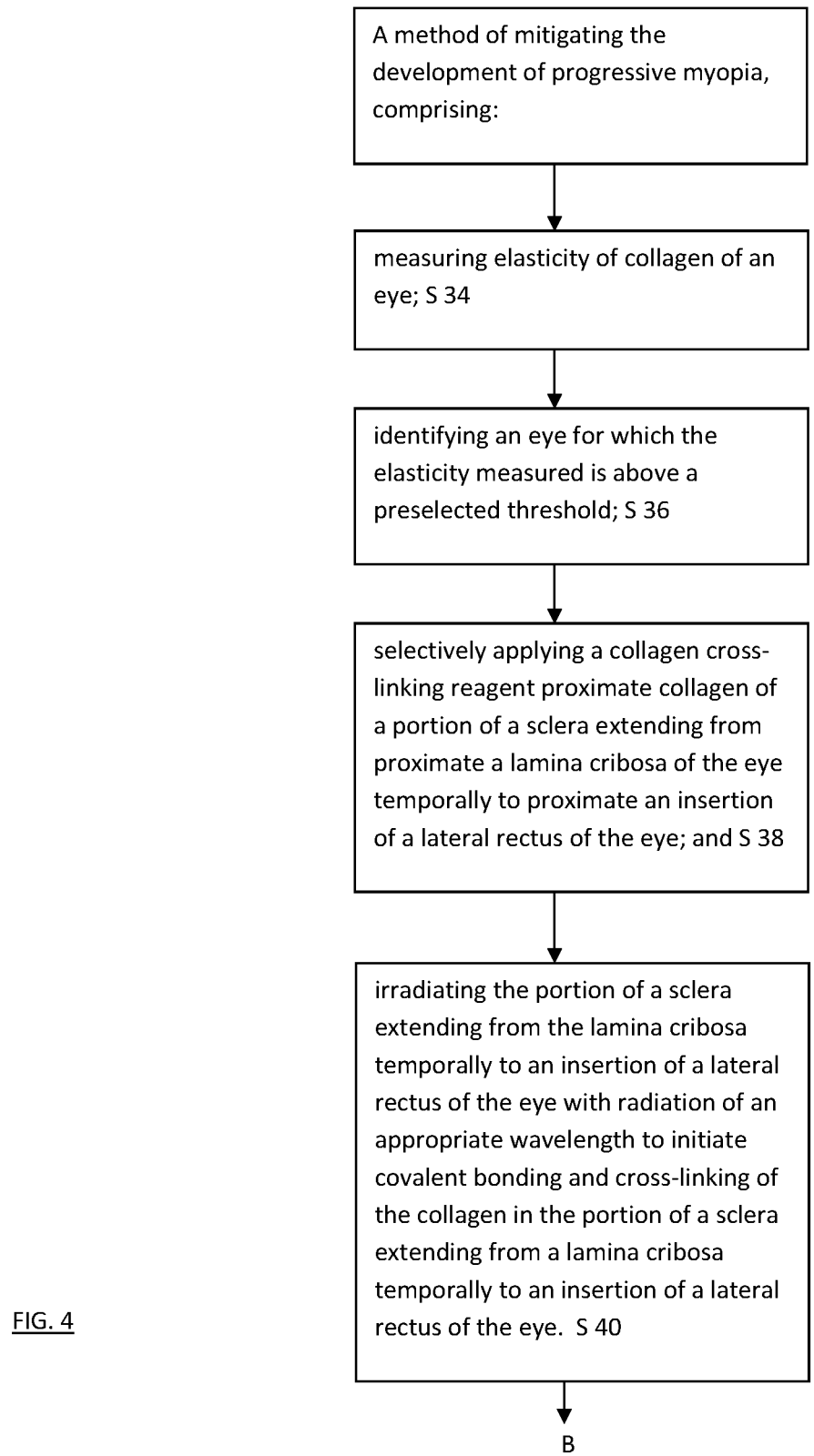
FIG. 4 is a flowchart of another method according to an example embodiment of the invention.
Figure 4:
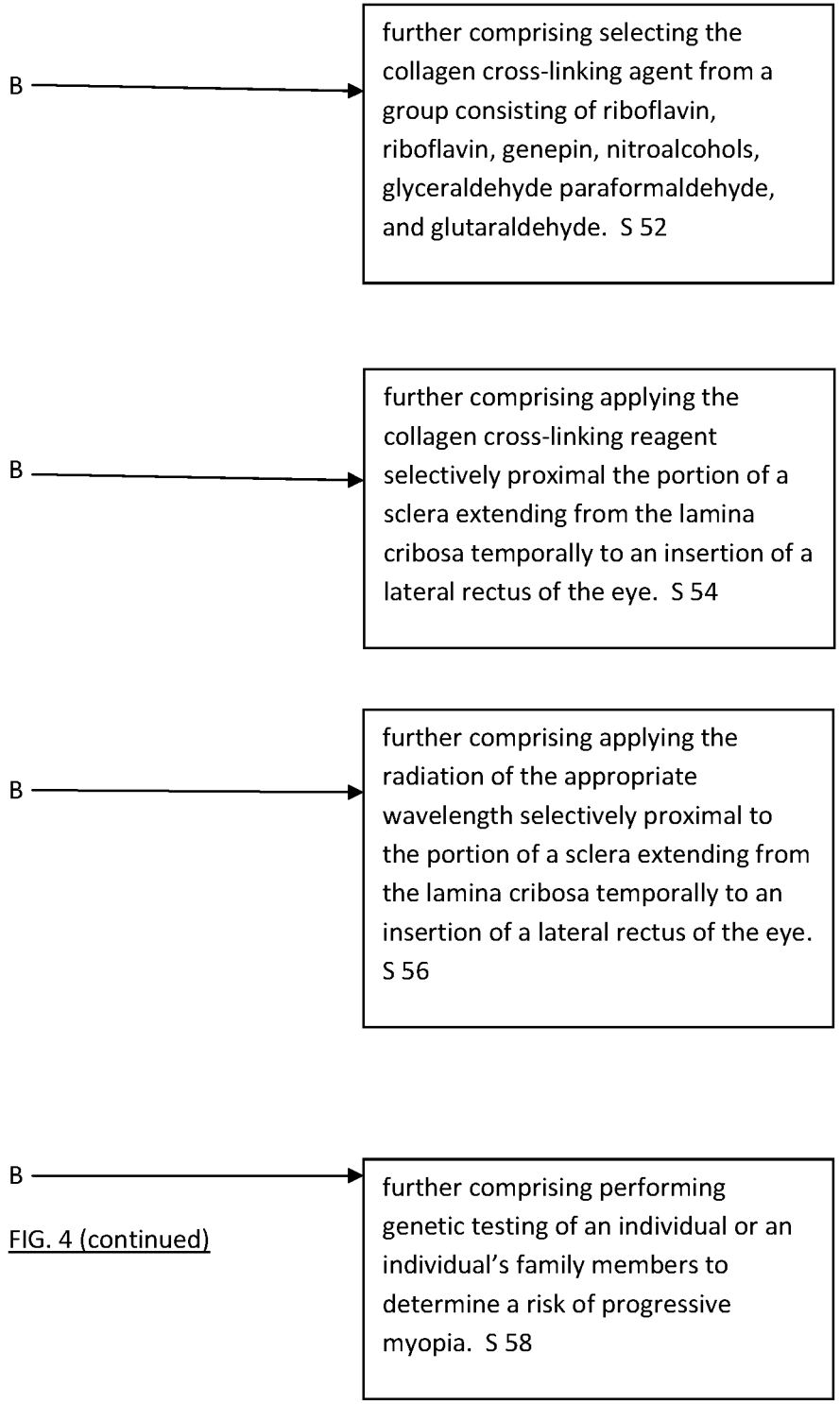
Figure 4:
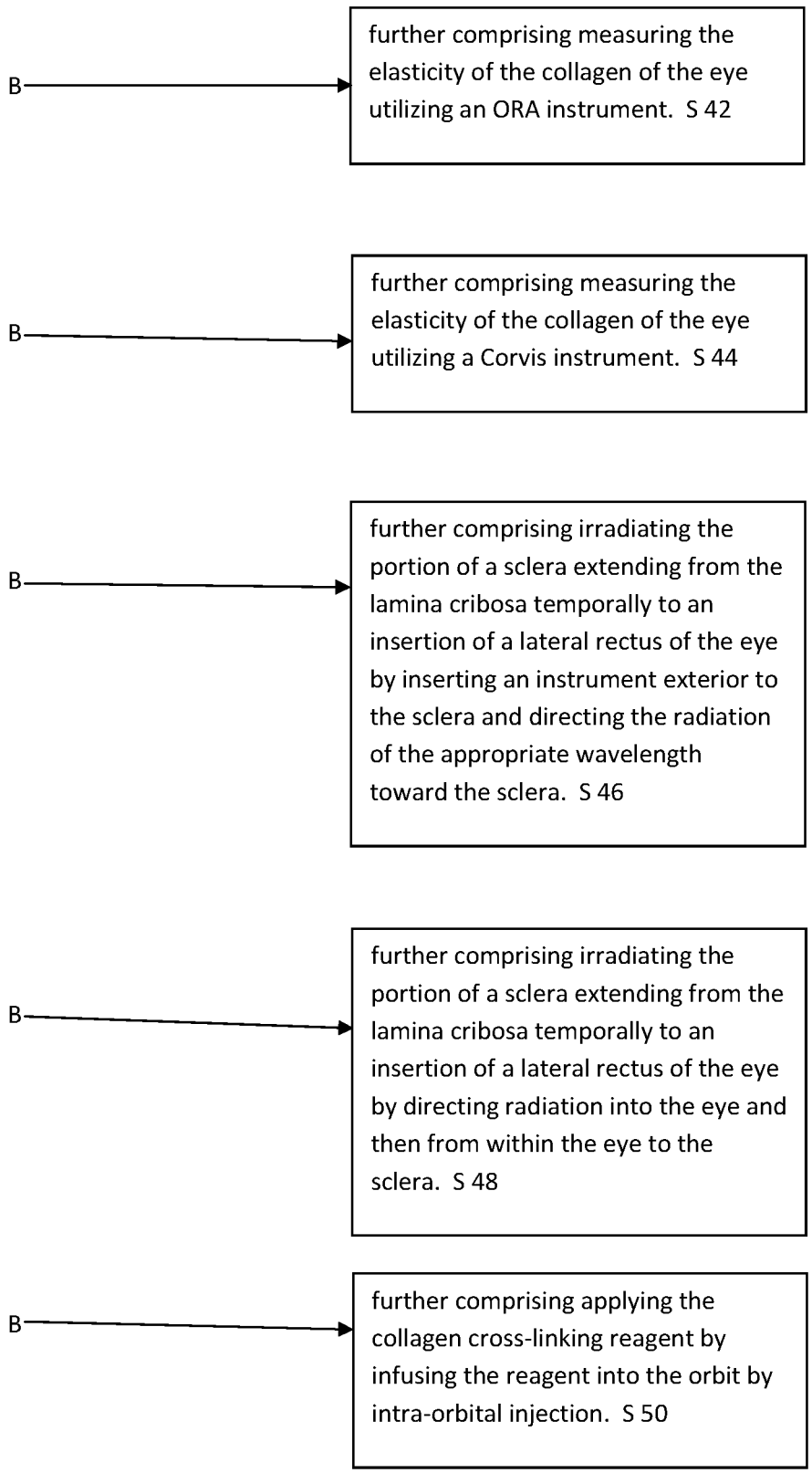

Referring to FIG. 3, according to a further example embodiment, the invention includes a method of mitigating the development of progressive myopia, including: measuring elasticity of collagen of eye 102 as shown in FIGS. 1, 2 and 3 S 10, identifying eye 102 for which the elasticity measured is above a preselected threshold; S 12 selectively applying a collagen cross-linking reagent proximate collagen of a portion of a sclera 116 extending from proximate a lamina cribrosa 122 of the eye temporally to proximate an insertion of a lateral rectus 132 of the eye; S 14 and irradiating the portion of a scleral 16 extending from the lamina cribrosa temporally to an insertion of a lateral rectus 132 of the eye with radiation of an appropriate wavelength to initiate covalent bonding and cross-linking of the collagen in the portion of a sclera 120 extending from a lamina cribrosa 122 temporally to an insertion of a lateral rectus 132 of the eye. S 16.

The application of collagen cross-linking selectively to the above discussed portions of globe 100 is expected to reduce elongation of globe 100 reducing the progression of axial myopia in much the same manner as cross-linking reduces the progression of keratoconus by reducing elasticity of collagen fibers.

Another example embodiment further includes measuring the elasticity of the collagen of the eye 102 utilizing an ORA instrument. S 18.

Another example embodiment further includes measuring the elasticity of the collagen of the eye 102 utilizing a Corvis instrument. S 20.

Another example embodiment further includes irradiating at least the posterior pole portion 124 of the eye 102 by inserting an instrument exterior to the sclera and directing the radiation of the appropriate wavelength toward the sclera. S 22.

Another example embodiment of the invention further includes irradiating at least the posterior pole portion 124 of the eye 102 by directing radiation into the eye and then from within the eye 102 to the sclera 120. S 24.

A further example embodiment of the invention further includes applying the collagen cross-linking reagent by infusing the reagent into the orbit by intra-orbital injection. S 26.

A further example embodiment additionally includes selecting the collagen cross-linking agent from a group consisting of riboflavin, riboflavin, genepin, nitroalcohols, glyceraldehyde paraformaldehyde, and glutaraldehyde. S 28.

Yet a further example embodiment further includes applying the collagen cross-linking reagent selectively proximal the posterior pole portion 124 of the eye and a temporal scleral portion 116 of the eye. S 30.

Another example embodiment of the invention further includes applying the radiation of the appropriate wavelength selectively proximal to the posterior pole portion 124 of the eye and a temporal scleral portion 116 of the eye. S 32.

Another example embodiment of the invention further includes performing genetic testing of an individual or an individual's family members to determine a risk of progressive myopia. S 33.

According to a further example embodiment, with reference to FIG. 5, the invention includes a method of mitigating the development of progressive myopia, including: measuring elasticity of collagen of an eye; S 34 identifying an eye for which the elasticity measured is above a preselected threshold; S 36 selectively applying a collagen cross-linking reagent proximate collagen of a portion of a sclera 120 extending from proximate a lamina cribrosa 122 of the eye temporally to proximate an insertion of a lateral rectus 132 of the eye; S 38 and irradiating the portion of a sclera 120 extending from the lamina cribrosa 122 temporally to an insertion of a lateral rectus 132 of the eye 102 with radiation of an appropriate wavelength to initiate covalent bonding and cross-linking of the collagen in the portion of a sclera 120 extending from a lamina cribrosa 122 temporally to an insertion of a lateral rectus 132 of the eye. S 40.

According to another example embodiment, the method includes measuring the elasticity of the collagen of the eye utilizing an ORA instrument. S 42.

According to another example embodiment, the method includes measuring the elasticity of the collagen of the eye 102 utilizing a Corvis instrument. S 44.

According to another example embodiment, the method includes irradiating the portion of a sclera 120 extending from the lamina cribrosa 122 temporally to an insertion of a lateral rectus 132 of the eye 102 by inserting an instrument exterior to the sclera and directing the radiation of the appropriate wavelength toward the sclera. S 46.

In a further example embodiment, the method includes irradiating the portion of a sclera 120 extending from the lamina cribrosa 122 temporally to an insertion of a lateral rectus 132 of the eye by directing radiation into the eye and then from within the eye to the sclera. S 48.

In a further example embodiment, the method includes applying the collagen cross-linking reagent by infusing the reagent into the orbit by intra-orbital injection. S 50. Infusing the reagent into the orbit and proximate the portion of sclera 120 desired to be treated may be accomplished by known techniques of intraorbital or retrobulbar injection.

In another example, the method includes selecting the collagen cross-linking agent from a group consisting of riboflavin, genepin, nitroalcohols, glyceraldehyde paraformaldehyde, and glutaraldehyde. S 52. This list should not be considered limiting. All other collagen cross-linking agents that may be available or may become available with time are considered to be within the scope of the invention.

In yet another example embodiment, the method includes applying the collagen cross-linking reagent selectively proximal the portion of a sclera 120 extending from the lamina cribrosa 122 temporally to an insertion of a lateral rectus 132 of the eye. S 54.

In a further example, the method includes applying the radiation of the appropriate wavelength selectively proximal to the portion of a sclera 120 extending from the lamina cribrosa 122 temporally to an insertion of a lateral rectus 132 of the eye. S 56.

Another example embodiment of the invention further includes performing genetic testing of an individual or an individual's family members to determine a risk of progressive myopia. S 58.

Radiation of the appropriate wavelength may be applied for example by insertion of an instrument having at its end for example light emitting diodes (LEDs) emitting the radiation of a desired wavelength. Further, an instrument having an optical fiber may be utilized to transmit radiation to the desired area.

Figure 6:
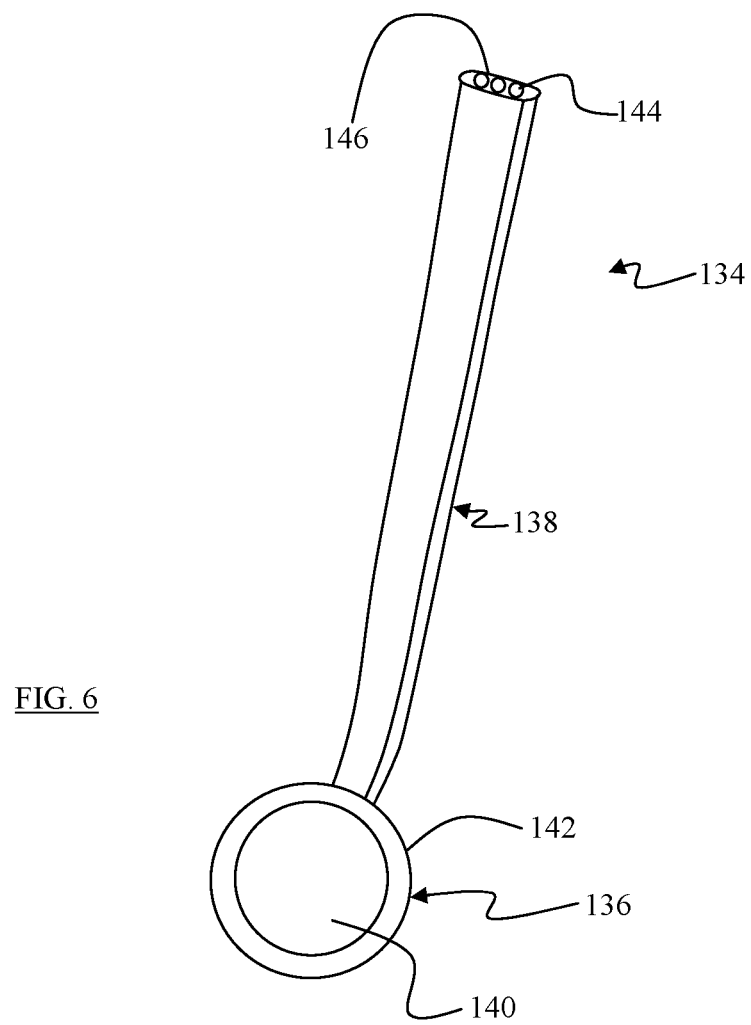
FIG. 6 is a schematic depiction of an instrument for applying the radiation of an appropriate wavelength to a sclera of an eye.

Referring to FIG. 6, irradiating instrument 134 generally includes irradiating head 136 and supporting handle 138.

Irradiating head 136 generally includes illumination emitter 140 and supporting ring 142. Illumination emitter 140 emits ultraviolet radiation of an appropriate wavelength to facilitate irradiating the portion of a sclera 120 extending from the lamina cribrosa 122 temporally to an insertion of a lateral rectus 132 of the eye 102 with radiation of an appropriate wavelength to initiate covalent bonding and cross-linking of the collagen in the portion of a sclera 120. Illumination emitter 140 may include for example light emitting diodes (LEDs) or a light emitting terminus of an optical fiber.

Supporting handle 138 may include for example optical fibers 144 or electrical conductors 146 to illuminate illumination emitter 140 including LEDs. Supporting handle 138 is sized and shaped to facilitate insertion into an orbit of eye 102 via a conjunctival incision.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of mitigating the development of myopia, comprising:
    measuring elasticity of collagen of an eye;
    identifying an eye for which the elasticity measured is above a preselected threshold;
    selectively applying a collagen cross-linking reagent proximate collagen of a sclera of a posterior pole portion of the eye for which the elasticity measured is above the preselected threshold; and
    irradiating at least the posterior pole portion of the eye with radiation of an appropriate wavelength to initiate covalent bonding and cross-linking of the collagen for which the elasticity measured is above the preselected threshold.

2. The method claimed in claim 1, further comprising measuring the elasticity of the collagen of the eye utilizing an instrument selected from a group consisting of an ORA instrument and a Corvis® instrument.

3. The method as claimed in claim 1, further comprising irradiating at least the posterior pole portion of the eye by inserting an instrument exterior to the sclera and directing the radiation of the appropriate wavelength toward the sclera.

4. The method as claimed in claim 1, further comprising irradiating at least the posterior pole portion of the eye by directing radiation into the eye and then from within the eye to the sclera.

5. The method as claimed in claim 1, further comprising applying the collagen cross-linking reagent by infusing the reagent into the orbit by intra-orbital injection.

6. The method as claimed in claim 1, further comprising selecting the collagen cross-linking agent from a group consisting of riboflavin, genepin, nitroalcohols, glyceraldehyde paraformaldehyde, and glutaraldehyde.

7. The method as claimed in claim 1, further comprising applying the collagen cross-linking reagent selectively proximal the posterior pole portion of the eye and a temporal scleral portion of the eye.

8. The method as claimed in claim 1, further comprising applying the radiation of the appropriate wavelength selectively proximal to the posterior pole portion of the eye and a temporal scleral portion of the eye.

9. The method as claimed in claim 1 further comprising performing genetic evaluation to determine a risk of progressive myopia.

10. A method of mitigating the development of progressive myopia, comprising:
    measuring elasticity of collagen of an eye;
    identifying an eye for which the elasticity measured is above a preselected threshold;
    selectively applying a collagen cross-linking reagent proximate collagen of a portion of a sclera extending from proximate a lamina cribrosa of the eye temporally to proximate an insertion of a lateral rectus of the eye; and
    irradiating the portion of a sclera extending from the lamina cribrosa temporally to an insertion of a lateral rectus of the eye with radiation of an appropriate wavelength to initiate covalent bonding and cross-linking of the collagen in the portion of a sclera extending from a lamina cribrosa temporally to an insertion of a lateral rectus of the eye.

11. The method claimed in claim 10, further comprising measuring the elasticity of the collagen of the eye utilizing an instrument selected from a group consisting of an ORA instrument and a Corvis® instrument.

12. The method as claimed in claim 10, further comprising irradiating the portion of a sclera extending from the lamina cribrosa temporally to an insertion of a lateral rectus of the eye by inserting an instrument exterior to the sclera and directing the radiation of the appropriate wavelength toward the sclera.

13. The method as claimed in claim 10, further comprising irradiating the portion of a sclera extending from the lamina cribrosa temporally to an insertion of a lateral rectus of the eye by directing radiation into the eye and then from within the eye to the sclera.

14. The method as claimed in claim 10, further comprising applying the collagen cross-linking reagent by infusing the reagent into the orbit by intra-orbital injection.

15. The method as claimed in claim 10, further comprising selecting the collagen cross-linking agent from a group consisting of riboflavin, genepin, nitroalcohols, glyceraldehyde paraformaldehyde, and glutaraldehyde.

16. The method as claimed in claim 10, further comprising applying the collagen cross-linking reagent selectively proximal the portion of a sclera extending from the lamina cribrosa temporally to an insertion of a lateral rectus of the eye.

17. The method as claimed in claim 10, further comprising applying the radiation of the appropriate wavelength selectively proximal to the portion of a sclera extending from the lamina cribrosa temporally to an insertion of a lateral rectus of the eye.

18. The method as claimed in claim 10, further comprising prescribing base in prism for an individual identified as being at rest for development of the progressive myopia.

19. The method as claimed in claim 18, further comprising prescribing the base in prism in a range of between 10 and 12 prism diopters.

20. The method as claimed in claim 10 further comprising performing genetic evaluation to determine a risk of progressive myopia.

* * * * *